(12) United States Patent
Leon-Yip

(10) Patent No.: US 10,441,404 B2
(45) Date of Patent: Oct. 15, 2019

(54) EMBOLECTOMY DEVICES

(71) Applicants: STRYKER CORPORATION, Kalamazoo, MI (US); STRYKER EUROPEAN HOLDINGS I, LLC, Kalamazoo, MI (US)

(72) Inventor: Garvin Leon-Yip, San Francisco, CA (US)

(73) Assignees: STRYKER CORPORATION, Kalamazoo, MI (US); STRYKER EUROPEAN HOLDINGS I, LLC, Kalamazoo, MI (US)

(*) Notice: Subject to any disclaimer, the term of this patent is extended or adjusted under 35 U.S.C. 154(b) by 117 days.

(21) Appl. No.: 15/270,635

(22) Filed: Sep. 20, 2016

(65) Prior Publication Data

US 2017/0079767 A1    Mar. 23, 2017

Related U.S. Application Data

(60) Provisional application No. 62/221,533, filed on Sep. 21, 2015.

(51) Int. Cl.
*A61F 2/01* (2006.01)
*A61B 17/221* (2006.01)
(Continued)

(52) U.S. Cl.
CPC .............. *A61F 2/01* (2013.01); *A61B 17/221* (2013.01); *A61B 2017/00477* (2013.01);
(Continued)

(58) Field of Classification Search
CPC ........ A61B 17/22031; A61B 17/22032; A61B 17/221; A61B 2017/22034; A61B 2017/22035; A61B 2017/2212; A61B 2017/2215; A61B 2017/2217; A61B 17/3207; A61B 17/320725;
(Continued)

(56) References Cited

U.S. PATENT DOCUMENTS 6,179,859 B1    1/2001    Bates et al.
6,544,279 B1    4/2003    Hopkins et al.
(Continued)

FOREIGN PATENT DOCUMENTS

DE    8707515 U1    7/1987
EP    2361590 A1    8/2011
WO    WO 2014/169266 A1    10/2014

OTHER PUBLICATIONS

PCT International Search Report and Written Opinion for International Appln. No. PCT/US2016/052651, Applicant Stryker Corporation, dated Nov. 23, 2016 (9 pages).

*Primary Examiner* — Katrina M Stransky
*Assistant Examiner* — Kankindi Rwego
(74) *Attorney, Agent, or Firm* — Vista IP Law Group LLP

(57) ABSTRACT

An embolectomy device includes a clot engaging structure comprising a plurality of interconnected struts forming an open cell structure, and further includes an attachment structure configured to advance and retract the clot engaging structure out of, and back into, respectively, the open distal end of a delivery catheter, the attachment structure comprising an elongated support member attached to one or more struts of the clot engaging structure only at locations on each of the respective one or more struts that are distal of a proximal end of the clot engaging structure.

11 Claims, 8 Drawing Sheets

(51) Int. Cl.
  *A61B 17/00* (2006.01)
  *A61B 17/22* (2006.01)
(52) U.S. Cl.
  CPC .......... *A61B 2017/2215* (2013.01); *A61B 2017/22034* (2013.01); *A61F 2002/011* (2013.01); *A61F 2002/016* (2013.01)
(58) Field of Classification Search
  CPC ... A61B 2017/2945; A61B 2017/32096; A61F 2/01; A61F 2/013; A61F 2/018; A61F 2/88; A61F 2/91; A61F 2/915; A61F 2/95; A61F 2002/825; A61F 2002/9528; A61F 2002/9534; A61F 2002/011; A61F 2002/015; A61F 2002/016; A61F 2002/018
  See application file for complete search history.

(56) References Cited

U.S. PATENT DOCUMENTS

| | | |
|---|---|---|
| 6,605,111 B2 | 8/2003 | Bose et al. |
| 6,610,077 B1 | 8/2003 | Hancock et al. |
| 6,652,548 B2 | 11/2003 | Evans et al. |
| 7,063,707 B2 | 5/2006 | Bose et al. |
| 7,399,308 B2 | 7/2008 | Borillo et al. |
| 7,862,578 B2 | 1/2011 | Tsugita |
| 7,883,526 B2 | 2/2011 | Jones et al. |
| 7,901,426 B2 | 3/2011 | Gilson et al. |
| 7,927,349 B2 | 4/2011 | Brady et al. |
| 8,062,328 B2 | 11/2011 | Hallisey |
| 8,337,520 B2 | 12/2012 | Cully et al. |
| 8,430,837 B2 | 4/2013 | Jenson et al. |
| 8,523,936 B2 | 9/2013 | Schmid et al. |
| 8,529,596 B2 | 9/2013 | Grandfield |
| 8,771,289 B2 | 7/2014 | Mohiuddin et al. |
| 8,777,976 B2 | 7/2014 | Brady et al. |
| 8,852,205 B2 | 10/2014 | Brady et al. |
| 2004/0049226 A1 | 3/2004 | Brady et al. |
| 2005/0267491 A1 | 12/2005 | Kellett et al. |
| 2007/0219642 A1 | 9/2007 | Richter |
| 2010/0268265 A1 | 10/2010 | Krolik et al. |
| 2011/0009941 A1 | 1/2011 | Grandfield et al. |
| 2012/0197285 A1 | 8/2012 | Martin et al. |
| 2012/0222969 A1 | 9/2012 | Osborne et al. |
| 2013/0030460 A1 | 1/2013 | Marks et al. |
| 2013/0060276 A1 | 3/2013 | Hocking |
| 2013/0131690 A1 | 5/2013 | Nagl et al. |
| 2014/0005674 A1 | 1/2014 | Angel et al. |
| 2014/0052103 A1 | 2/2014 | Cully et al. |

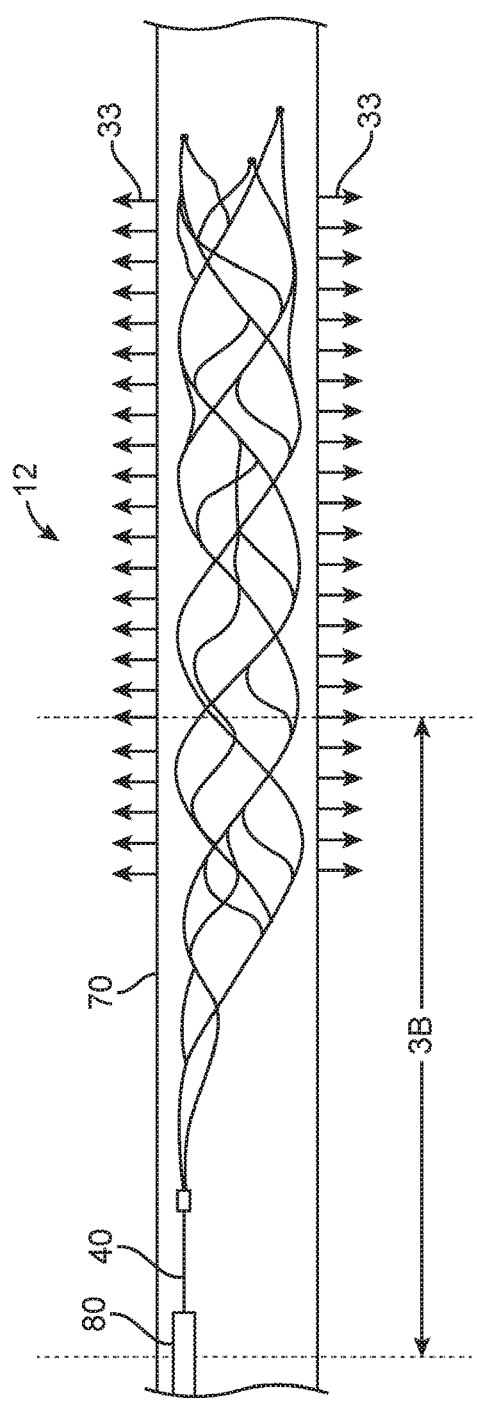
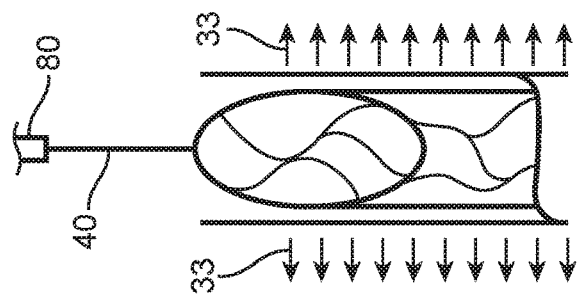
FIG. 3A (PRIOR ART)
FIG. 3B (PRIOR ART)

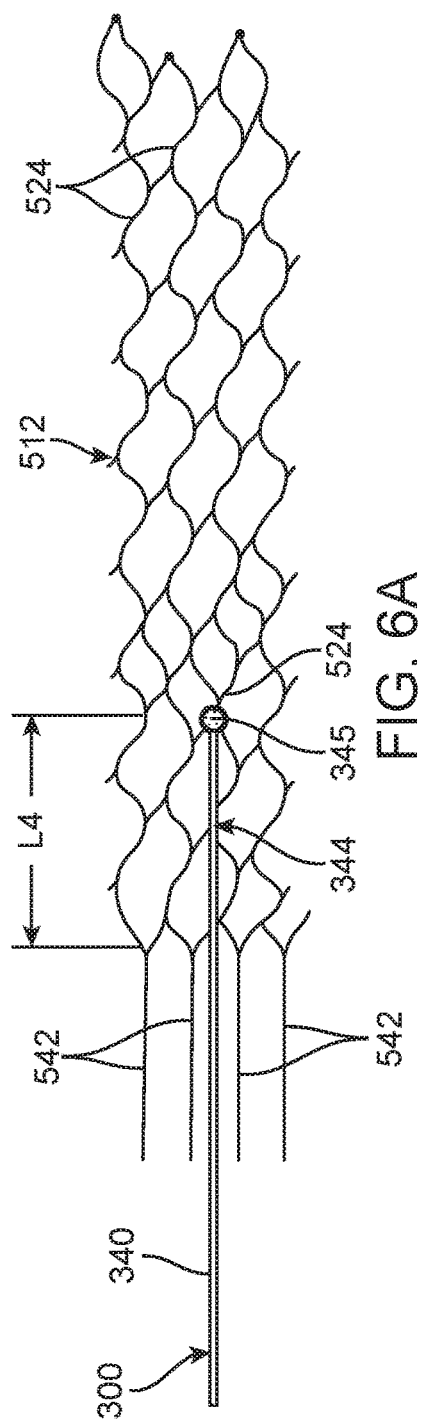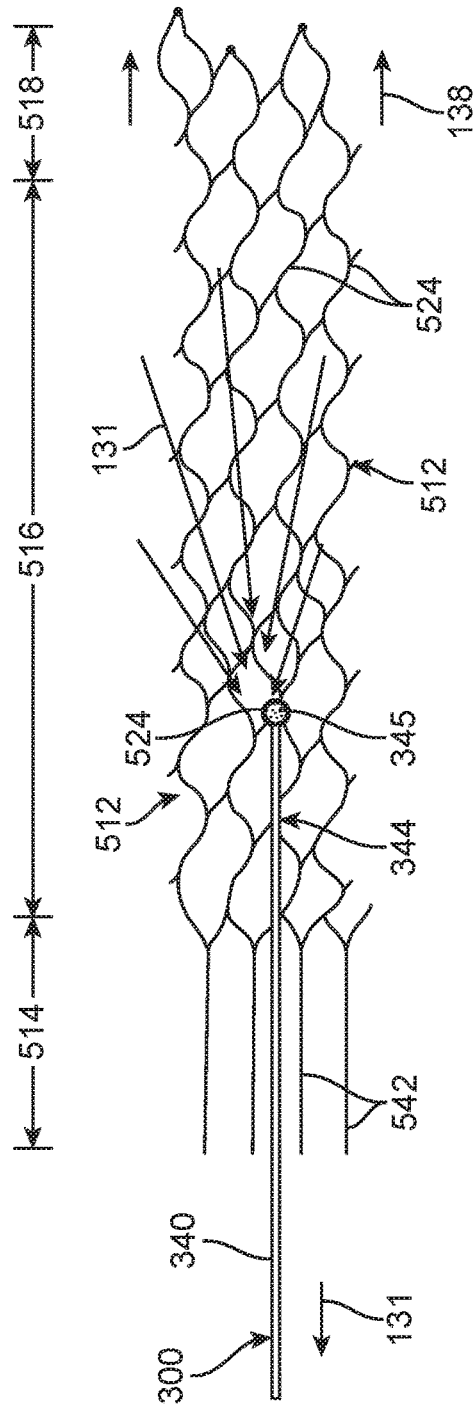

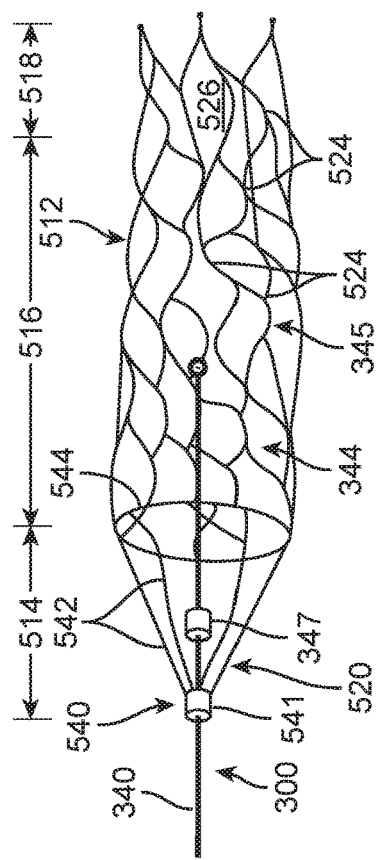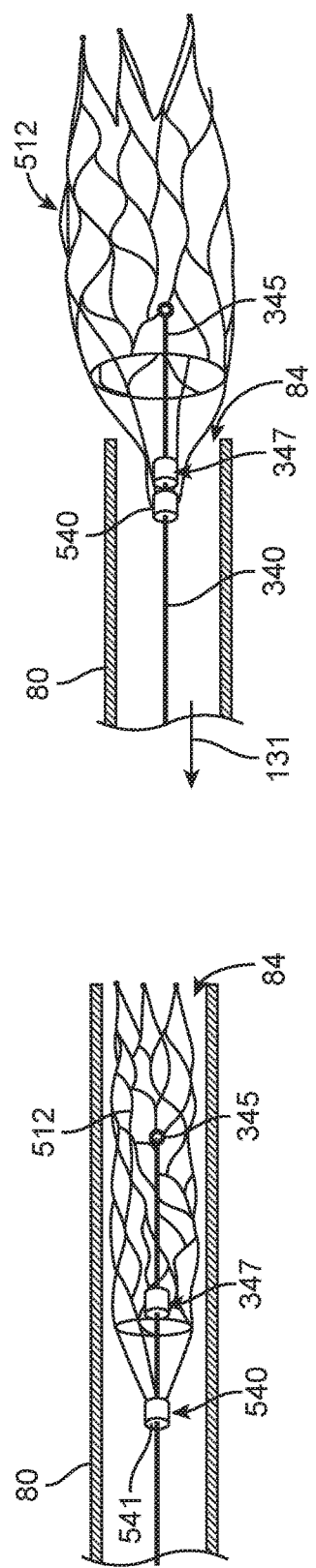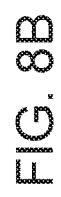

EMBOLECTOMY DEVICES

RELATED APPLICATION DATA

The present application claims the benefit under 35 U.S.C. § 119 to U.S. provisional patent application Ser. No. 62/221,533, filed Sep. 21, 2015. The foregoing application is hereby incorporated by reference into the present application in its entirety.

FIELD OF INVENTION

The inventions disclosed herein relate generally to medical devices for removing embolic obstructions from the vasculature.

BACKGROUND

Blood thrombus, embolus or clots may occur in a person's vasculature system. Sometimes such clots are harmlessly dissolved in the blood stream. Other times, however, such clots may lodge in a blood vessel, where they can partially or completely occlude the flow of blood, referred to as an ischemic event. If the partially or completely occluded vessel feeds blood to sensitive tissue such as, in the brain, lungs, or heart, serious tissue damage may result. Such ischemic events may also be exacerbated by atherosclerosis, a vascular disease that causes the vessels to become narrowed and/or tortuous. The narrowing and/or increased tortuosity of the blood vessels may, in certain circumstances, lead to the formation of atherosclerotic plaque that can cause further complications.

Known embolectomy devices may be used in a variety of applications to remove blood clots or other foreign objects from blood vessels. Such devices include cylindrical scaffold embolectomy devices, such as those illustrated and described in U.S. Pat. No. 8,529,596 to Grandfield, the contents of which are fully incorporated herein by reference. FIGS. 1A-B illustrate an exemplary prior art embolectomy device 12 that is manufactured and sold by the Neurovascular Intervention Division of Stryker Corp. (http://www.stryker.com/en-us/products/Neurovascular-Intervention/index.htm). FIG. 1A shows the embolectomy device 12 in a two-dimensional plane view, and FIG. 1B shows the device 12 a three-dimensional expanded tubular configuration. The embolectomy device 12 is composed of shape memory, self-expandable and biocompatible materials, such as Nitinol. The embolectomy device 12 is preferably manufactured by laser cutting a tube or a sheet of shape memory material. The embolectomy device 12 is coupled to an elongate flexible wire 40 at a proximal end 20 of the device 12. The wire 40 extends proximally from device 12 and is configured to advance and withdraw the embolectomy device 12 through sheaths, catheters and/or patient's vasculature into a target site in a blood vessel. To enhance visibility of the device 12 (e.g., under fluoroscopy) during advancement and withdrawal within the vasculature, the device 12 may be fully or partially coated with a radiopaque material, such as tungsten, platinum, platinum/iridium, tantalum and gold. Alternatively or in conjunction with the use of a radiopaque coating, radiopaque markers 60 may be disposed at or near the proximal end 20 and/or the distal end 22 of the device 12.

As shown in FIG. 1A, the embolectomy device 12 includes a proximal end portion 14, a main body portion 16 and a distal end portion 18, the main body portion including a plurality of longitudinal undulating elements 24 (e.g., wires, struts) with adjacent undulating elements being out-of-phase with one another and connected in a manner to form a plurality of diagonally disposed cell structures 26 extending between the respective proximal and distal end portions of the device. The cell structures 26 in the main body portion 16 and distal end portion 18 of the embolectomy device 12 extend continuously and circumferentially around a longitudinal axis 30 of the device 12 (FIGS. 1A-B).

In particular, the cell structures 26 in the proximal end portion 14 extend less than circumferentially around the longitudinal axis 30 of the device 12. The dimensional and material characteristics of the cell structures 26 of the main body portion 16 are selected to produce sufficient radial force (e.g., radial force per unit length of between 0.005 N/mm to 0.1 N/mm, preferable between 0.030 N/mm to 0.050 N/mm) and contact interaction to cause the cell structures 26, and/or the elements 24, to engage with an embolic obstruction residing in the vasculature in a manner that permits partial or full removal of the embolic obstruction from the patient. As best seen in FIG. 1B, the embolectomy device 12 comprises a lumen 35 and an axial length L1 of about 32 millimeters with the main body portion 16 length L2 measuring about 20 millimeters. The length L2 of the main body portion 16 is generally between about 2.5 to about 3.5 times greater than the length of the proximal end portion 14. Usually, the length L2 is considered the effective length of the device 12 when radial forces are acting upon the deployed device 12 (FIG. 3C) for engagement of embolic obstructions disposed within the vasculature.

FIG. 2 illustrates the embolectomy device 12 of FIGS. 1A-B disposed in a target site of a tortuous vascular anatomy of a patient for capturing an embolic obstruction or clot 75. In an unexpanded or radially compressed configuration (not shown), such as when the embolectomy device 12 is disposed within a delivery catheter 80, the embolectomy device 12 has an unexpanded outer diameter (UOD) between 0.4 to 0.7 millimeters. In a radially expanded configuration (FIGS. 1B-2), the embolectomy device 12 has an expanded outer diameter (EOD) between 2.5 to 5.0 millimeters.

The embolectomy device 12 produces sufficient radial force and contact interaction to cause the strut elements 24 and/or cell structures 26 to engage, snare, encapsulate, capture, pinch and/or entrap the embolic obstruction 75 disposed within a tortuous vasculature, such as blood vessel 70, allowing removal of the embolic obstruction 75 from the patient. The diameter of the main body portion 16 in a fully expanded configuration is about 4.0 millimeters with the cell pattern, elements 24 dimensions and material being selected to produce a radial force of between 0.040 N/mm to 0.050 N/mm when the diameter of the main body portion is reduced to between 1.0 millimeters to 1.5 millimeters. The cell pattern 26, strut dimensions 24 and material(s) are selected to produce a radial force of between 0.010 N/mm to 0.020 N/mm when the diameter of the main body portion 16 is reduced to 3.0 millimeters. Having a strut thickness to width ratio of greater than one promotes integration of the strut elements 24 into the embolic obstruction 75.

Regardless of the technique used to manufacture the embolectomy device 12, the manner in which the strut elements 24 interconnect determines the device's longitudinal and radial rigidity and flexibility. Radial rigidity is needed to provide the radial force needed to engage the clot or embolic obstruction 75, but radial flexibility is needed to facilitate radial compression of the device 12 for delivery into a target site. Longitudinal rigidity is needed to pull, retrieve or withdraw an engaged clot or embolic obstruction 75 from the blood vessel 70, but longitudinal flexibility is needed to facilitate delivery of the device 12 (e.g., through tortuous vasculature).

Embolectomy device 12 patterns are typically designed to maintain an optimal balance between longitudinal and radial rigidity and flexibility for the device 12. However, after deployment of the device 12 into the blood vessel 70 to radially expand into a predetermined diameter, as shown in FIGS. 3A-B, the device 12 is subjected to tensions and forces when withdrawn, as shown in FIG. 3D (i.e., withdrawal force depicted by arrows 31; compressive force depicted by arrows 36; resistance force depicted by arrows 38). In certain applications, the interaction of said forces 31, 36, 38 on the device 12 tend to create a tapered profile 37 reducing the expanded outer diameter (EOD) and the lumen 35 of the device 12 (FIGS. 3C-D).

The tapered profile 37, formed by the compression of the struts 24 when the device 12 is withdrawn, is created at the proximal end portion 14, and usually extends to the main body portion 16 of the device 12, as shown in FIGS. 3C-D. The withdrawal force 31 is exerted to the device 12 through the wire 40 that is attached to the proximal end 20 of the device 12 (FIGS. 1A-B, 2 and 3A-D), which in turn subjects the device 12 to compressive force 36 causing the tapered profile 37, including a reduction on the effective length L2 of the device 12, depicted as a reduced effective length L3 in FIGS. 3C-D. When the device 12 is subjected to the withdrawal force 31, the contact of the device 12 with the blood vessel wall and/or the embolic obstruction produces the resistance force 38 that contributes to the compression and tapered profile 37 of the device 12. As shown in FIG. 3C, the reduced effective length L3 is about 25% smaller than the effective length L2 (reduced percentage shown as "%<L2"). In certain embodiments, the reduced effective length L3 may be 25% to 50% smaller than the effective length L2 (not shown).

The withdrawal 31, compressive 36, and/or resistance 38 forces or combination thereof that cause compression of the struts 24 when the device 12 is withdrawn, and thereby causing the tapered profile 37, reduced effective length L3 and reduced lumen 35 (shown in FIGS. 3C-D) tend to squeeze out the captured embolic obstruction 75 from the device 12, usually, out of the tapered profile 37 and/or the distal end portion 14 of the device 12 (shown in FIG. 4). The squeezed out embolic obstruction 75 or parts thereof, may disengage from the device 12, migrate into other portions of the vasculature within the body, where they can partially or completely occlude the flow of blood. If the partially or completely occluded vessel feeds blood to sensitive tissue such as, the brain, lungs or heart, for example, serious tissue damage, organ failure or death may result.

Accordingly, it would be desirable to prevent compressed tapered profile and reduced effective length of embolectomy devices that may squeeze out captured embolic obstructions into the vasculature of a patient when the device is subjected to withdrawal forces.

SUMMARY

In an exemplary embodiment of the disclosed inventions, an embolectomy device comprises a clot engaging structure including a plurality of interconnected struts forming an open cell structure having a proximal end, and an attachment structure configured to advance and retract the clot engaging structure out of, and back into, respectively, a distal opening of a delivery catheter within a targeted blood vessel. The attachment structure comprises an elongated support member attached to one or more struts of the clot engaging structure only at locations on each of the respective one or more struts that are distal of the proximal end of the clot engaging structure, so that withdrawal forces are exerted to the locations distal of the proximal end of the clot engaging structure when retracted.

In various embodiments, the one or more struts comprise a plurality of struts of the clot engaging structure attached to the elongated support member. The one or more struts of the clot engaging structure are directly attached to the elongated support member. The attachment structure further comprises a distal end coupler connected to the elongated support member, wherein the one or more struts of the clot engaging structure are attached to the distal end coupler and thereby indirectly attached to the elongated support member. The elongated support member comprises a flexible wire.

Further, the clot engaging structure has an axial length, when the most proximal attachment location of any strut to the elongated support member is distal of at least about twenty percent of the axial length of the clot engaging structure. The location of the most proximal attachment point of any strut of the clot engaging structure to the elongated support member is at or approximately at a midpoint of the axial length of the clot engaging structure.

In any of the embodiments described above, a plurality of struts defining the proximal end of the clot engaging structure are connected to a proximal end connector ring having a lumen through which the elongated support member extends. The proximal end connector ring comprises or is otherwise coupled to a radiopaque marker. The elongated support member is translatable relative to the proximal end connector ring, the attachment structure further comprising a bumper fixedly attached to the elongated support member distal of the proximal end connector ring, such that the bumper prevents translation of the elongated support member in a proximal direction relative to the clot engaging structure beyond a relative position in which the bumper engages the proximal end connector ring.

Other and further aspects and features of embodiments of the disclosed inventions will become apparent from the ensuing detailed description in view of the accompanying figures.

BRIEF DESCRIPTION OF THE DRAWINGS

FIGS. 3A-D are respective perspective and plan views of the prior art embolectomy device of FIGS. 1A and 1B, depicted while being subjected to respective radial, withdrawal and compressive forces.

FIGS. 6A and 6B are respective plan views of an embolectomy device constructed according to another embodiment of the disclosed inventions.

FIG. 7 is a perspective view of the embolectomy device of FIGS. 6A and B, and

FIGS. 8A and 8B are perspective views of the embolectomy device of FIG. 7, and also depicting a delivery catheter according to the disclosed inventions.

DETAILED DESCRIPTION OF THE ILLUSTRATED EMBODIMENTS

Figure 1A:
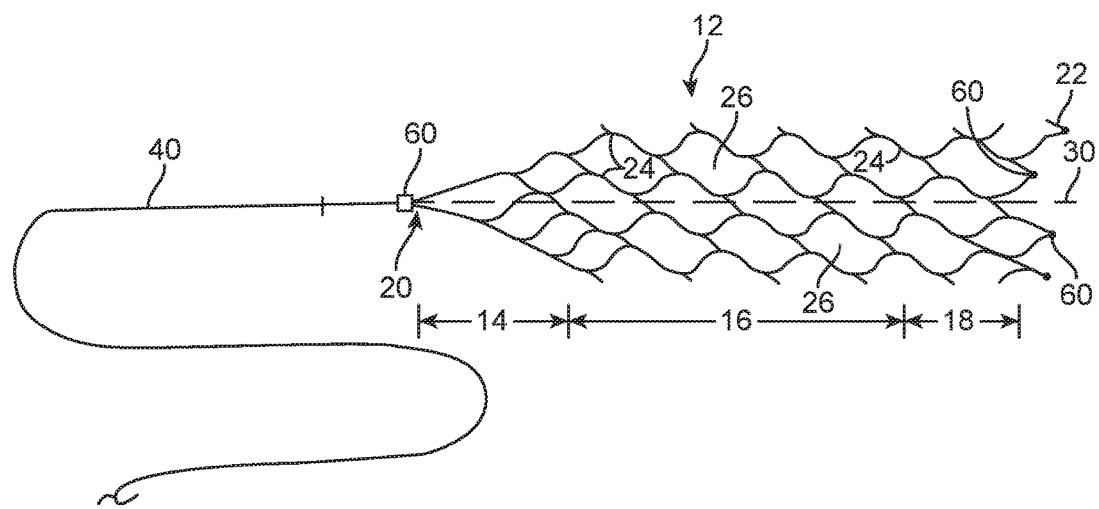
FIGS. 1A and 1B are respective perspective and plan views of a prior art embolectomy device.
Figure 1B:
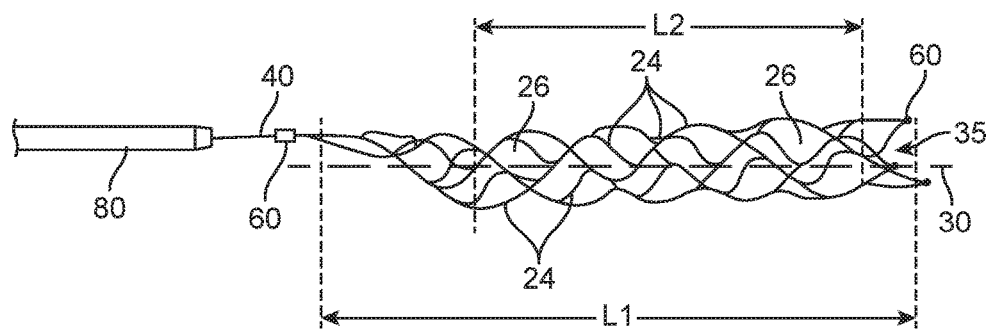
Figure 2:
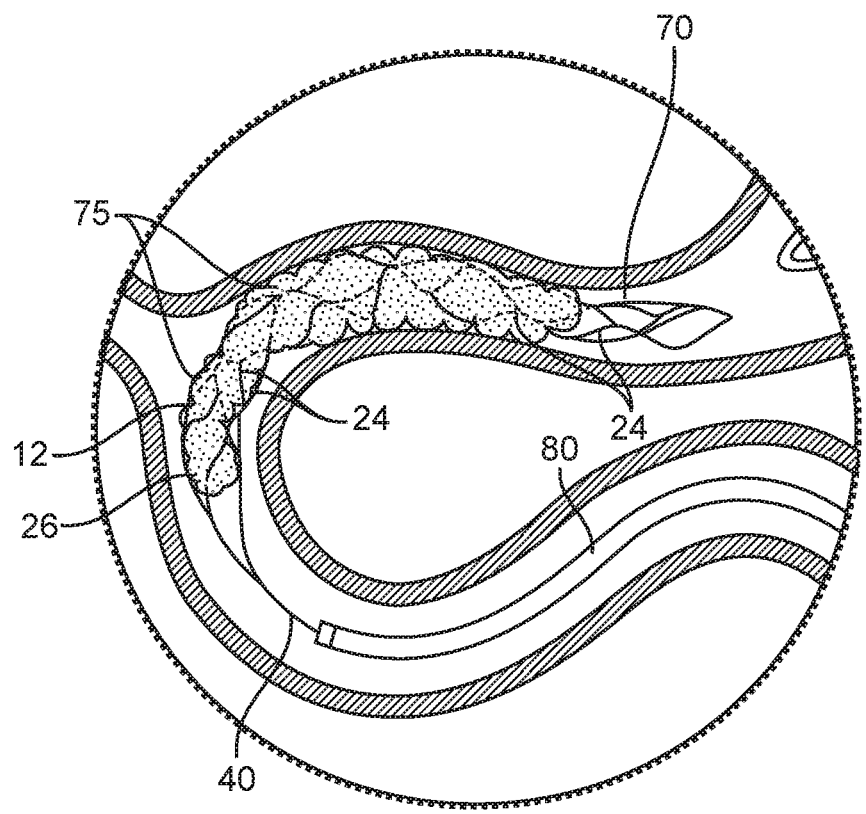
FIG. 2 is a perspective view of the prior art embolectomy device shown in FIGS. 1A and 1B, depicted capturing an embolic obstruction within a tortuous blood vessel.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Figure 5:
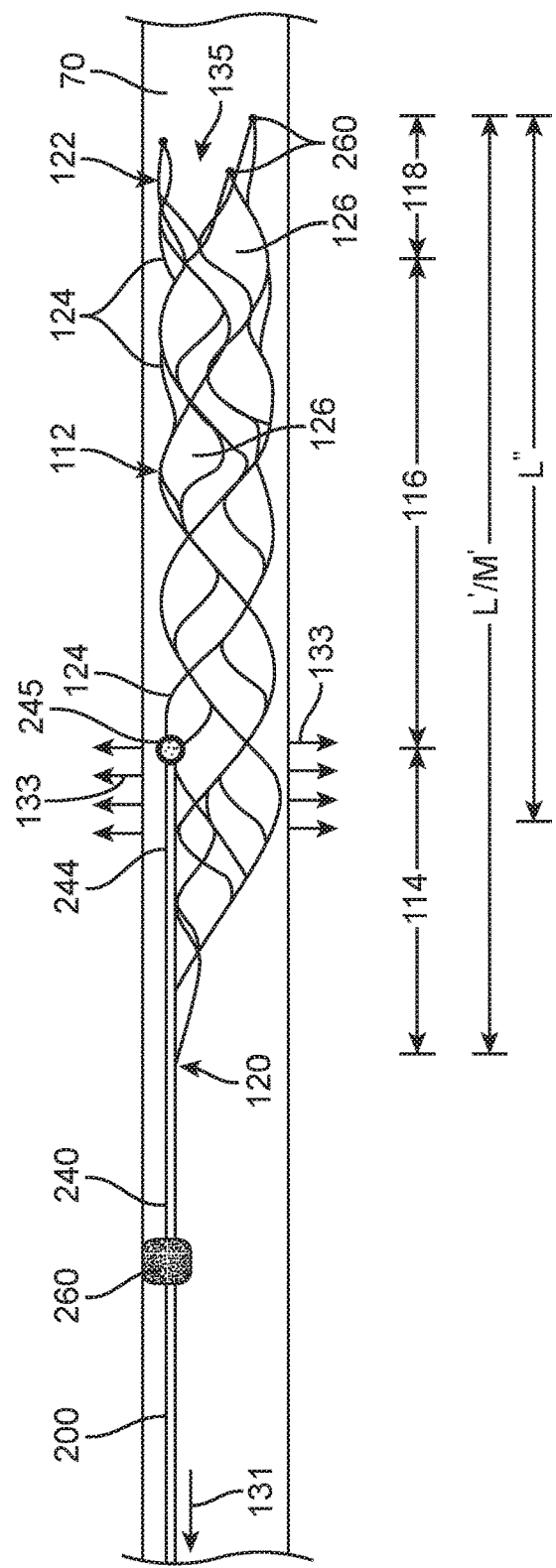
FIG. 5 is a perspective view of an embolectomy device constructed according to one embodiment of the disclosed inventions.

FIG. 5 illustrates an attachment structure 200 for embolectomy devices, constructed in accordance with one embodiment of the disclosed inventions. The attachment structure 200 includes an elongated member 240, such as a push wire, flexible wire, or the like. The elongated support member 240 includes a proximal portion (not shown) and a distal portion 244; the distal portion 244 may include a distal end coupler 245. The embolectomy device 112 also referred to as, the clot engaging structure, has a proximal end portion 114, a main body portion 116 and a distal end portion 118. The embolectomy device 112 comprises a lumen 135 and an axial length L', and the main body portion 116 comprises an effective length L". The clot engaging structure 112 comprises a plurality of longitudinal undulating elements 124 (e.g., wires, struts) with adjacent undulating elements being out-of-phase with one another and connected in a manner to form a plurality of diagonally disposed open cell structures 126 extending between the respective proximal 114 and distal 118 end portions of the device 112. The clot engaging structure 112 is coupled to the elongated support member 240 at one or more struts elements 124 of the device 112 (e.g., direct attachment) or at the distal end coupler 245 of the elongated support member 240 (e.g., indirect attachment via a coupler that is attached to one or more struts). The embolectomy device 112 is composed of shape memory, self-expandable and biocompatible materials, such as Nitinol. The embolectomy device 112 is preferably manufactured by laser cutting a tube or a sheet of shape memory material.

The elongated support member 240 extends proximally from device 112 and is configured to advance and withdraw the embolectomy device 112 through sheaths, catheters and/or patient's vasculature into a target site in a blood vessel 70. Particularly, the elongated support member 240 is configured to advance the embolectomy device 112 out of a distal opening of a delivery catheter within a targeted blood vessel, and configured to withdraw the device 112 into the distal opening of the delivery catheter. To enhance visibility of the device 112 (e.g., under fluoroscopy) during advancement and withdrawal within the vasculature, the device 112 may be fully or partially coated with a radiopaque material, such as tungsten, platinum, platinum/iridium, tantalum and gold. Alternatively or in conjunction with the use of a radiopaque coating, radiopaque markers 260 may be disposed at or near a proximal end 120 and/or at the distal end 122 of the device 112.

The elongated support member 240 is coupled to the clot engaging structure 112 (i.e., directly or indirectly) for example, by adhesive, thermal bonding, welding or the like, or combinations thereof, or by any other suitable methods. It should be appreciated that when referring to the distal end coupler 245 (i.e., indirect attachment), the suitable features, configurations and effects of the coupler 245 may also apply to the one or more strut elements 124 (i.e., direct attachment) of the embolectomy device 112 attached to the elongated support member 240.

The coupler 245 is coupled to the embolectomy device 112 at one or more strut elements 124 of the device/structure 112 (FIG. 5). In one embodiment, the coupler 245 is fixedly attached or secured to the one or more strut elements 124 of the device 112. Additionally, the coupler 245 may be coupled to one or more strut elements 124 along the length of the distal portion (not shown). For example, the distal portion 244 of the elongated support member 240 may be slidably coupled to the one or more struts elements 124, so that when the device 112 is withdrawn, a greater percentage or majority of the withdrawal forces 131 are exerted to the location where the coupler 245 is coupled to the embolectomy device 112.

Figures 3C, 3D:
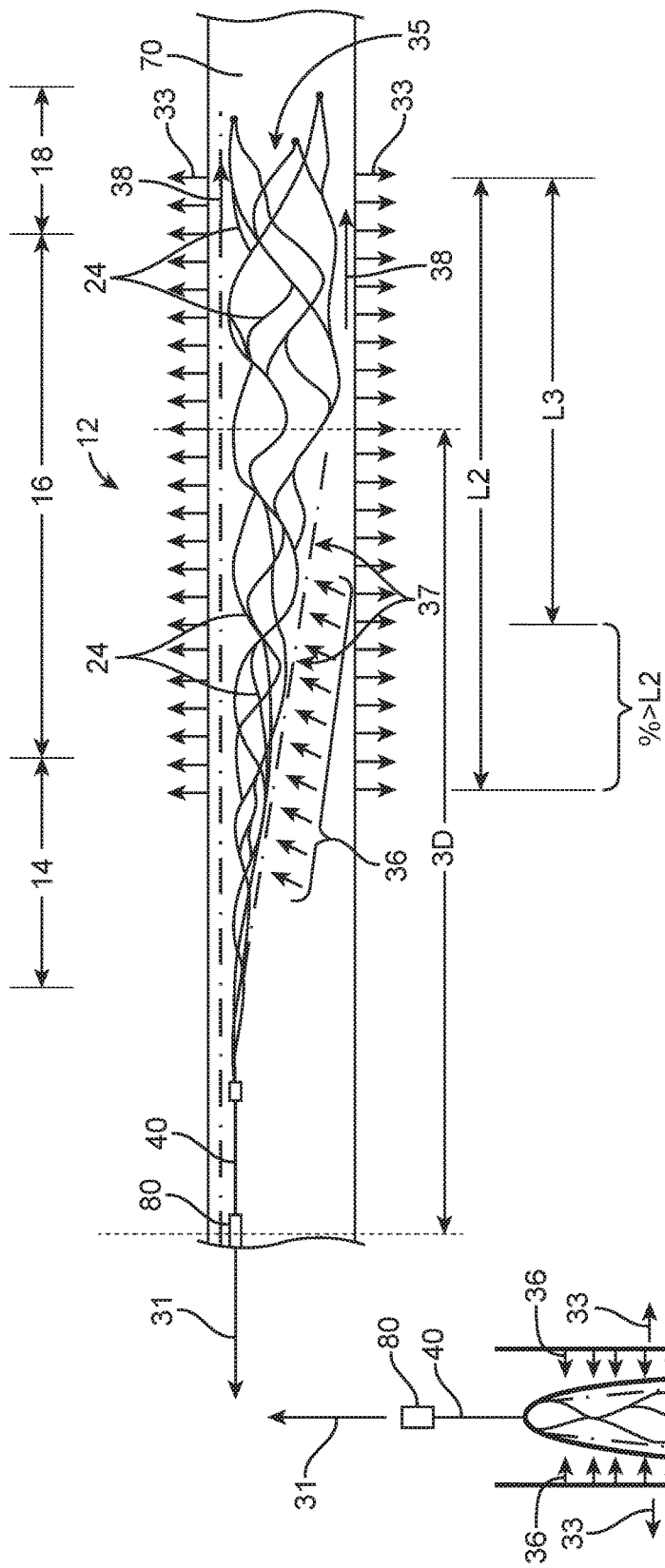
Figure 4:
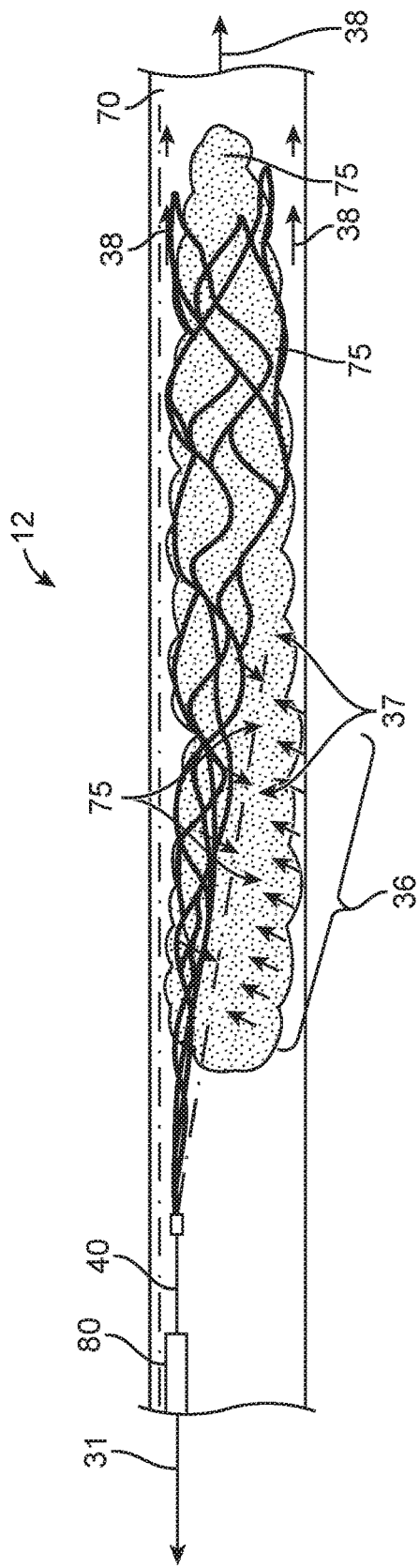
FIG. 4 is a perspective view of the prior art embolectomy device of FIGS. 1A and 1B, depicted after having a captured embolic obstruction and while being subjected to withdrawal force.

The distal end coupler 245 is coupled to the embolectomy device 112 at a location distally disposed from the proximal end 120 of the device 112 and/or proximately disposed from a section of the device 112 subjected to radial force 133 when deployed, as shown in FIG. 5. In one embodiment, the coupler 245 is coupled to the embolectomy device 112 between the proximal end portion 114 and the main body portion 116, as long as the coupler 245 is proximately disposed to some radial force 133 exerted to the device 112, so that the coupler 245 allows withdrawal of the device 112 while avoiding and/or substantially minimizing the formation of the compressed tapered profile shown in FIGS. 3C-4. In other embodiments, the coupler 245 may be coupled to the embolectomy device 112 at the main body portion 116. For example, the coupler 245 may be coupled to the embolectomy device 112 at the proximal end portion 114, as long as the coupler 245 is not disposed at the proximal end 120 of the device 112.

Having the coupler 245 of the elongated member 240 coupled to the embolectomy device 112 at a location distally disposed from the proximal end 120 of the device 112 (FIG. 5), allows for the radial force 133 to be retained at the proximal end portion 114 of the device, while avoiding and/or substantially minimizing the formation of the compressed tapered profile and/or a reduced effective length of embolectomy device 112 (FIGS. 3C-4) that tends to squeezed out captured embolic obstructions into the vasculature of a patient when the device 112 is subjected to withdrawal forces 131. The coupler 245 is configured to transmit a greater percentage of the withdrawal forces 131 to the location where the coupler 245 is attached to the embolectomy device 112. Even if one or more strut elements 124 may be also be coupled to the distal end 244 of the elongated member 240, the greater percentage of the withdrawal forces 131 are exerted to the device 112 via the coupler 245.

In one embodiment, the most proximal attachment location of any struts 124 (or via the coupler 245) to the elongated support member 240 is distal of at least about twenty percent of the axial length L' of the device 112. Alternatively, the most proximal attachment location of any struts 124 (or via the coupler 245) to the elongated support member 240 is at or approximately at a midpoint M' of the axial length L' of the device 112.

It should be appreciated that the attachment structure 200, elongated support member 240 at the distal end coupler 245, may have an alternative shapes, and other suitable configurations. Other variations of the support structure 200, such as the configuration of the elongated support member 240 and the distal end coupler 245 (e.g., locations, shapes, materials), may be contemplated, in which some exemplary configurations are depicted in FIGS. 6A-8B. As used in this specification, the term "attachment structure" may refer to any device or component to which one or more components may be directly or indirectly coupled, attached or secured. Further, as used in this specification, the term "coupled" may refer to one or more components that may be directly or indirectly attached, secured, or otherwise, connected.

The attachment structure 200 may be composed from any number of biocompatible, compressible, elastic materials or combinations thereof, including polymeric materials, metals, and metal alloys, such as stainless steel, tantalum, or a nickel titanium alloy such as a super-elastic nickel titanium alloy known as Nitinol. The attachment structure 200 may include radio-opaque markers or be coated with a layer of radiopaque materials. The embolectomy device 112 can be woven from wires, cut out of tubes, or cut out of sheets using a variety of techniques, including laser cutting or etching a pattern onto a tube or sheet to form struts from the remaining material, or other suitable techniques. The embolectomy device 112 may be composed from any number of biocompatible, compressible, elastic materials or combinations thereof, including polymeric materials, metals, and metal alloys, such as stainless steel, tantalum, or a nickel titanium alloy such as a super-elastic nickel titanium alloy known as Nitinol.

FIGS. 6A-B illustrate an attachment structure for embolectomy devices, constructed in accordance with another embodiment of the disclosed inventions. The attachment structure 300 includes an elongated support member 340 having a proximal portion (not shown) and a distal portion 344, the distal portion 344 including a distal end coupler 345. The distal end coupler 345 is coupled to an embolectomy device 512 at a location distally disposed from the proximal end 514 of the device 512, as shown in FIGS. 6A-B and 7. At the proximal end portion 514, the embolectomy device 512 includes a plurality of elongated struts 542 extending from the struts 524. Additionally, the plurality of extending struts 542 may be coupled to a flexible support frame 544 (FIGS. 7, 8A-B).

It should be appreciated that when referring to the distal end coupler 345 (i.e., indirect attachment), the suitable features, configurations and effects of the coupler 345 may also apply to the one or more strut elements 524 (i.e., direct attachment) of the embolectomy device 512 attached to the elongated support member 340. The distal end coupler 345 of the elongated support member 340 is coupled to embolectomy device 512 at one or more strut elements 524 of the device 512. Additionally, the distal portion 344 of the elongated support member 340 may be slidably coupled to one or more strut elements 524 along a length L4 of the distal portion 344 (FIG. 6A). Even if one or more strut elements 524 are coupled along the length L4 of the distal end 344 of the elongated support member 340, the coupler 345 is configured to transmit a greater percentage or the majority of the withdrawal forces 131 to the location where the coupler 345 is coupled to the embolectomy device 512, as shown in FIG. 6B. In this manner, when the embolectomy device 512 of FIGS. 6A-B is subjected to withdrawal forces 131 and/or resistance forces 138, the undesirable compressed tapered profile and/or a reduced effective length, described above (FIGS. 3C-4), would be avoided and/or substantially minimized in the device 512.

FIG. 7 illustrate the attachment structure for embolectomy devices, constructed in accordance with the embodiment of FIGS. 6A-B. The attachment structure 300 includes the elongated support member 340, such as a push wire, flexible wire, or the like. The elongated support member 340 includes the proximal portion (not shown) and the distal portion 344, the distal portion 344 including the distal end coupler 345 and a proximal bumper 347 fixedly coupled to the elongated support member 340. The embolectomy device 512 is coupled to the elongated support member 340 at the distal end coupler 345.

The embolectomy device 512 includes the proximal end portion 514, a main body portion 516 and a distal end portion 518, the main body portion 516 including a plurality of longitudinal undulating elements 524 (e.g., wires, struts) with adjacent undulating elements being out-of-phase with one another and connected in a manner to form a plurality of diagonally disposed cell structures 526 extending between the respective proximal 514 and distal 518 end portions of the device 512. The proximal end portion 514 of the device 512 may include a funnel-like, conical or other suitable configuration.

At the proximal end portion 514, the embolectomy device 512 includes an annular member 540 (e.g., connector ring, band, link or the like) coupled to the plurality of extending struts 542. The plurality of extending struts 542 may be coupled to a flexible support frame 544. The frame 544 may include a circular, oval or other suitable configuration. The annular member also referred to as connector ring 540, comprises a lumen 541 through which the elongated support member 340 extends, so that the annular member 540 is slidably disposed and axially translates relative to the elongated support member 340. The annular member 540 is proximately disposed to the bumper 347 of the member 340. The annular member 540 is configured to engage the bumper 347, as described in further detail below. The annular member 540 may comprise a radio-opaque markers, be composed of or be coated with a layer of radiopaque materials. The annular member 540, extending struts 542 and frame 544 may be formed of a unitary component (e.g., laser cut of cylindrical structure or sheet, 3D printing, extrusion or the like), our may also include separate components that are welded, bonded or otherwise engaged to one another.

The elongated support member 340 extends proximally from device 512 and is configured to advance and withdraw the embolectomy device 512 through sheaths, catheters and/or patient's vasculature into a target site in a blood vessel. The distal end coupler 345 of the elongated support member 340 is coupled to embolectomy device 512, for example, by adhesive, thermal bonding, welding or the like, or combinations thereof, or by any other suitable methods. The coupler 345 is coupled to the device 512 at one or more strut elements 524 of the embolectomy device 512, and at a location distally disposed from the proximal end 520 of the device 512, as shown in FIG. 7. The coupler 345 may be coupled to the embolectomy device 512 at the proximal end portion 514 or in 516, as long as the coupler 345 is not disposed at the proximal end 520 of the device 512.

FIGS. 8A-B illustrates the interface of the attachment structure for embolectomy devices, constructed in accordance the embodiment of FIGS. 6A-B and 7 with a delivery catheter. The embolectomy device 512 comprises a delivery configuration (FIG. 8A), in which the device 512 is radially compressed by a delivery catheter 80. The embolectomy device 512 comprises a deployed configuration (FIG. 8B) when the device 512 is advanced distally relative to the catheter 80, or the catheter 80 is withdrawn proximally relative to the embolectomy device 512 (or some of each), in order to deploy the device 512 out of the catheter 80 distal opening 84 and into the blood vessel, allowing the no-longer radially constrained embolectomy device 512 to radially expand to a predetermined diameter within the blood vessel.

In certain circumstances, the embolectomy device 512 should be re-sheathed into the delivery catheter 80 for repositioning and/or withdrawal of the device, before or after capturing an embolic obstruction. As shown in FIG. 8B, when withdrawal forces 131 are exerted through the elongate member 340, the coupler 345 is configured to transmit a greater percentage of the withdrawal forces 131 to the location where the coupler 345 is secured to the embolectomy device 512. Withdrawing the elongate member 340 also causes the bumper 347 to engage the annular member 540 of the device, guiding the extending struts 542 into the distal opening 84 of the catheter 80 for re-sheathing, retrieval or withdrawal of the embolectomy device 512. Since a majority of the withdrawal forces 131 are exerted to the embolectomy device 512 at the coupling (i.e., directly to the one or more struts 524 or indirectly via the coupler 345), when the embolectomy device 512 of FIGS. 6A-8B is withdrawn, the undesirable compressed tapered profile and/or a reduced effective length, described above (FIGS. 3C-4), would be avoided and/or substantially minimized in the device 512, preventing captured embolic obstructions from disengaging out of the embolectomy device 512 (not shown), as described above in conjunction with FIG. 4.

It will be appreciated that the attachment structures depicted in FIGS. 5-8B may be used in other suitable medical devices, for example, disposed within tubular prosthesis, implants, stents, fluid diverters or the like for both vascular and non-vascular applications.

While embodiments have been shown and described, various modifications may be made without departing from the scope of the inventive concepts disclosed herein. The invention(s), therefore, should not be limited, except as defined in the following claims.

What is claimed is:

1. An embolectomy device, comprising:
   a delivery catheter having a lumen in communication with an open distal end;
   a clot engaging structure comprising a plurality of interconnected struts forming an open cell structure, the open cell structure comprising a plurality of diagonally disposed cell structures, the clot engaging structure having a proximal end portion that terminates at a proximal end; and
   an attachment structure configured to advance and retract the clot engaging structure out of, and back into, respectively, the distal end opening of the delivery catheter within a targeted blood vessel, the attachment structure comprising an elongated support member attached to one or more struts of the clot engaging structure, the elongated support member having a distal end portion that terminates at a distal end,
   wherein the distal end of the elongated support member is attached to one or more struts of the clot engaging structure only at locations on each of the respective one or more struts that are distal of the proximal end of the clot engaging structure, so that withdrawal forces are exerted to the locations distal of the proximal end of the clot engaging structure when retracted.

2. The embolectomy device of claim 1, wherein the one or more struts comprise a plurality of struts of the clot engaging structure attached to the elongated support member.

3. The embolectomy device of claim 1, wherein the elongated support member comprises a flexible wire.

4. The embolectomy device of claim 1, wherein the one or more struts of the clot engaging structure are directly attached to the elongated support member.

5. The embolectomy device of claim 1, the attachment structure further comprising a distal end coupler connected to the elongated support member, wherein the one or more struts of the clot engaging structure are attached to the distal end coupler and thereby indirectly attached to the elongated support member.

6. The embolectomy device of claim 1, the clot engaging structure having an axial length, when the most proximal attachment location of any strut to the elongated support member is distal of at least about twenty percent of the axial length of the clot engaging structure.

7. The embolectomy device of claim 6, when the location of the most proximal attachment point of any strut of the clot engaging structure to the elongated support member is at or approximately at a midpoint of the axial length of the clot engaging structure.

8. The embolectomy device of claim 1, wherein a plurality of struts defining the proximal end of the clot engaging structure are connected to a proximal end connector ring having a lumen through which the elongated support member extends.

9. The embolectomy device of claim 8, wherein the proximal end connector ring comprises or is otherwise coupled to a radiopaque marker.

10. The embolectomy device of claim 8, wherein the elongated support member is translatable relative to the proximal end connector ring, the attachment structure further comprising a bumper fixedly attached to the elongated support member distal of the proximal end connector ring, such that the bumper prevents translation of the elongated support member in a proximal direction relative to the clot engaging structure beyond a relative position in which the bumper engages the proximal end connector ring.

11. The embolectomy device of claim 1, wherein the withdrawal forces from the elongated support member do not collapse the cell structures and/or reduce a profile of the clot engaging structure.

* * * * *